United States Patent
Rostami et al.

(10) Patent No.: US 9,867,907 B2
(45) Date of Patent: Jan. 16, 2018

(54) SELF-LUBRICATED CATHETERS

(71) Applicant: Hollister Incorporated, Libertyville, IL (US)

(72) Inventors: Shamsedin Rostami, South Cambridgeshire (GB); Joel D. Shutt, Gurnee, IL (US)

(73) Assignee: Hollister Incorporated, Libertyville, IL (US)

( * ) Notice: Subject to any disclaimer, the term of this patent is extended or adjusted under 35 U.S.C. 154(b) by 337 days.

(21) Appl. No.: 14/418,359

(22) PCT Filed: Jul. 26, 2013

(86) PCT No.: PCT/US2013/052269
§ 371 (c)(1),
(2) Date: Jan. 29, 2015

(87) PCT Pub. No.: WO2014/022227
PCT Pub. Date: Feb. 6, 2014

(65) Prior Publication Data
US 2015/0258247 A1    Sep. 17, 2015

Related U.S. Application Data

(60) Provisional application No. 61/677,733, filed on Jul. 31, 2012.

(51) Int. Cl.
*A61M 25/00* (2006.01)
*A61L 29/04* (2006.01)
(Continued)

(52) U.S. Cl.
CPC .......... *A61L 29/041* (2013.01); *A61L 29/049* (2013.01); *A61L 29/06* (2013.01); *A61L 29/14* (2013.01);
(Continued)

(58) Field of Classification Search
CPC .. A61M 2025/0046; A61M 2025/0047; A61M 25/0009; A61M 25/0017; A61M 2025/0062; C08F 222/06
See application file for complete search history.

(56) References Cited

U.S. PATENT DOCUMENTS 5,538,510 A * 7/1996 Fontirroche ...... A61M 25/0009
604/265
5,554,120 A * 9/1996 Chen .................... A61L 29/049
525/166
(Continued)

FOREIGN PATENT DOCUMENTS

CA    2388863 A1    5/2001
EP    0166998 A2    1/1986
(Continued)

OTHER PUBLICATIONS

Fusabond functional polymer. DuPont Company. http://www.dupont.com/products-and-services/plastics-polymers-resins/ethylene-copolymers/brands/fusabond-functional-polymers.html. Accessed Fri Aug. 25, 2017.*

(Continued)

*Primary Examiner* — Adam Marcetich
(74) *Attorney, Agent, or Firm* — Cook Alex Ltd.

(57) ABSTRACT

A catheter assembly includes at least one self-lubricated part formed from a mixture including a polymer and lubricant. The polymer has a functional group that can react with the functional group of the lubricant. The suitably functionalized lubricant provides for a low coefficient of friction surface for easier and less traumatic insertion and withdrawal of the catheter into and from body cavities.

28 Claims, 3 Drawing Sheets

(51) Int. Cl.
  *A61L 29/06* (2006.01)
  *A61L 29/14* (2006.01)
  *C08F 222/06* (2006.01)
(52) U.S. Cl.
  CPC ......... *A61L 2400/10* (2013.01); *C08F 222/06* (2013.01)

(56) References Cited

U.S. PATENT DOCUMENTS

| | | | | |
|---|---|---|---|---|
| 6,242,503 B1* | 6/2001 | Kozma | ............... | C08F 8/00 521/134 |
| 6,403,231 B1* | 6/2002 | Mueller | ............... | B32B 27/20 428/338 |
| 6,475,633 B1* | 11/2002 | Robert | ............... | B32B 7/12 428/476.9 |
| 2005/0119414 A1* | 6/2005 | Sasagawa | ............... | C08F 8/00 525/242 |
| 2005/0177133 A1* | 8/2005 | Nielsen | ............... | A61F 5/453 604/544 |
| 2005/0194718 A1* | 9/2005 | Blades | ............... | F16L 55/1656 264/269 |
| 2006/0147412 A1* | 7/2006 | Hossainy | ............... | C08B 37/0072 424/78.27 |
| 2008/0045665 A1* | 2/2008 | Chino | ............... | C08L 101/08 525/329.7 |
| 2009/0088711 A1* | 4/2009 | Shelley | ............... | A61M 1/008 604/328 |
| 2010/0049146 A1* | 2/2010 | Nielsen | ............... | A61L 17/145 604/265 |
| 2010/0119833 A1* | 5/2010 | Madsen | ............... | A61L 27/34 428/413 |
| 2010/0330315 A1* | 12/2010 | Robert | ............... | C09J 123/0884 428/35.7 |
| 2012/0164195 A1* | 6/2012 | Zheng | ............... | A61Q 19/00 424/401 |
| 2014/0030536 A1* | 1/2014 | Krishnaswamy | ............... | B32B 27/36 428/483 |

FOREIGN PATENT DOCUMENTS

| | | |
|---|---|---|
| EP | 0476401 A1 | 3/1992 |
| WO | WO 0234165 A1 | 5/2002 |

OTHER PUBLICATIONS

Subsequent Canadian Office Action dated Jan. 20, 2017, for Application No. 2,880,526 entitled: Self-Lubricated Catheters.
Notification of Transmittal of the International Search Report, International Search Report and Written Opinion for PCT/US2013/052269 dated Oct. 17, 2013.
Canadian Office Action dated Apr. 8, 2016, for Application No. 2,880,526 entitled: Self-Lubricated Catheters.

* cited by examiner

SELF-LUBRICATED CATHETERS

The present application is a U.S. National Stage of PCT International Patent Application No. PCT/US2013/052269, filed Jul. 26, 2013, which claims the benefit of and priority to U.S. Provisional Patent Application No. 61/677,733, filed Jul. 31, 2012, both of which are hereby incorporated herein by reference.

BACKGROUND

The present disclosure relates to catheters, and more particularly to self-lubricated urinary catheters.

Intermittent catheterization is a good option for many users who suffer from various abnormalities of the urinary system. Urinary catheter systems typically include a long, thin, flexible tube (the urinary catheter) that is inserted into the urethra, past the trigone muscle and into the bladder to withdraw urine from the bladder. Urine flows through the catheter and is collected, e.g., in a urine collection bag.

It is common for catheters to be lubricated to reduce friction in order to allow for easier and less traumatic insertion and withdraw. Currently, there are two major categories of catheters having lubricated surfaces, i.e., gel lubricated catheters and hydrophilic coated catheters.

Gel lubricated catheters are made easier to insert and withdraw by application of lubricant (typically a water-based lubricant) on the catheter surface. A catheter can be supplied with lubricant pre-applied on the catheter surface just before or during the packaging operation. Alternatively, lubricant can be applied on the catheter surface by a user as the catheter is being inserted. However, the handling of the gel lubricated catheter by the user can be messy, leaving lubricant on the user's hands. Further, it can increase the risk of infection from microorganisms being introduced into the body through handling of the gel lubricated catheter.

In a hydrophilic coated catheter, the catheter is provided with a thin hydrophilic coating which is applied to the outer surface of the catheter. The coating is activated by swelling when in contact with a hydrating agent such as liquid water, water vapor, combinations thereof and the like, and provides an extremely low coefficient of friction surface. The most common form of this product is one in which a sterile, individually packaged, single use catheter is provided in a dry state or condition. The user opens the package, pours water into the package, waits a predetermined period of time, for example, 30 seconds, and then removes the catheter from the package which is ready for insertion. Some hydrophilic coated catheters are provided in a package that contains enough liquid water to cause it to be immersed, or is provided with water necessary for immersion of the catheter in a separate water packet within the package.

One disadvantage of the hydrophilic coated catheters is that the immersion liquid has a tendency to spill from the package as the user handles the catheter and tries to remove it from the package for subsequent insertion. Further, special packaging requirements increase the complexity of such catheter systems. Another disadvantage of the hydrophilic coated catheter is that the catheter has an extremely slippery surface which makes it quite difficult for the user to handle during insertion.

Therefore, there is a need for improved catheters having a lubricious surface without a tendency to spill. The present disclosure provides improved catheters according to various embodiments to provide an alternative lubricated surface.

BRIEF SUMMARY

A self-lubricated catheter or a catheter assembly including at least one self-lubricated part is provided according to various embodiments. Unlike previously introduced catheters that use lubricant or a lubricious coating, the self-lubricated catheter or the self-lubricated parts are formed from a mixture including a polymer and a lubricant to provide a low coefficient of friction surface for an easy and less traumatic insertion and withdraw of the catheter. The lubricant can be selected from a functionalized lubricant family.

In one aspect, a catheter formed from a mixture is provided. The mixture includes an amine containing lubricant in an amount between about 0.05 percent by weight (wt. %) and about 20 wt. %, and a polymer. The polymer may contain functional groups that can react with the lubricant to retain it. For example, amine containing lubricants can react with maleic anhydride containing polymers in a molten state. Other functional groups, such as hydroxyl and acid groups, can also be used. The maleic anhydride can be grafted onto the polymer, such as maleic anhydride grafted ethylene propylene copolymers, or copolymerized, such as ethylene-co-vinylacetate-co-maleic anhydride copolymers (EVA-MA polymer), with maleic anhydride contents of about 1% to about 30%.

In one embodiment, the catheter is formed from a mixture including an EVA-MA polymer in an amount of about 90 wt. % to about 99 wt. % and an oleamide based lubricant in an amount of about 1 wt. % to about 10 wt. %. Preferably, the mixture includes the EVA-MA polymer in an amount of about 95 wt. % and the oleamide based lubricant in an amount of about 5 wt. %.

In another embodiment, the catheter is formed from a mixture including an EVA-MA polymer in an amount of about 90 wt. % to about 99 wt. % and an erucamide in an amount of about 1 wt. % to about 10 wt. %. Preferably, the mixture includes the EVA-MA polymer in an amount of about 95 wt. % and the erucamide in an amount of about 5 wt. %.

In yet another embodiment, the catheter is formed from a mixture including an EVA-MA polymer in an amount of about 90 wt. % to about 99 wt. % and an ethylene bis-oleamide in an amount of about 1 wt. % to about 10 wt. %. Preferably, the mixture includes the EVA-MA polymer in an amount of about 95 wt. % and the ethylene bis-oleamide in an amount of about 5 wt. %.

Preferably, any of the above described catheters have an outer surface having a coefficient of friction of less than about 0.3, more preferably less than about 0.2 when measured according to modified ASTM D1894.

In another aspect, a multilayer catheter is provided. The multilayer catheter includes an outer layer and an inner layer. The outer layer is formed from a mixture including an amine containing lubricant in an amount of about 1 wt. % to about 20 wt. %., and a first polymer having a functional group that reacts with an amine functional group of the amine containing lubricant. The inner layer is formed from a second polymer. Preferably, the first polymer is an EVA-MA polymer. The second polymer can be EVA without MA, or any other polymers that has suitable adhesion with the outer layer, such as polyvinylchloride, polyurethane, and suitably functionalized thermoplastic elastomers.

In one embodiment, the outer layer is formed from a mixture including an EVA-MA polymer in an amount of about 90 wt. % to about 99 wt. % and an oleamide in an amount of about 1 wt. % to about 10 wt. %. Preferably, the mixture includes the EVA-MA polymer in an amount of about 95 wt. % and the oleamide in an amount of about 5 wt. %.

In another embodiment, the outer layer is formed from a mixture including an EVA-MA polymer in an amount of about 90 wt. % to about 95 wt. % and a erucamide in an amount of about 1 wt. % to about 10 wt. %. Preferably, the mixture includes the EVA-MA polymer in an amount of about 95 wt. % and the erucamide in an amount of about 5 wt. %.

In yet another embodiment, the outer layer is formed from a mixture including an EVA-MA polymer in an amount of about 90 wt. % to about 99 wt. % and an ethylene bis-oleamide in an amount of about 1 wt. % to about 10 wt. %. Preferably, the mixture includes the EVA-MA polymer in an amount of about 95 wt. % and the ethylene bis-oleamide in an amount of about 5 wt. %.

Preferably, the outer layer of the multilayer catheter has a coefficient of friction of less than about 0.3, and more preferably less than about 0.2 when measured according to modified ASTM D1894. Preferably, the second polymer is selected from the group consisting of EVA-MA polymer, ethylene-co-vinylacetate polymer, thermoplastic polyurethane polymer, amide-ethylene oxide copolymers, and thermoplastic olefin elastomer.

In one aspect, a catheter assembly including at least one self-lubricated part is provided. The at least one self-lubricated part includes a functionalized polymer containing a first functional group, and a functionalized lubricant containing a second functional group that can react with the first functional group. The functionalized polymer and the functionalized lubricant are melt mixed to form a mixture, which is used to make the at least one self-lubricated part.

In one embodiment, the functionalized polymer is an anhydride functionalized polymer, and the functionalized lubricant is an amine functionalized lubricant. Preferably, the mixture includes the amine functionalized lubricant in an amount of about 0.05 wt. % to about 20 wt. %. One preferred functionalized polymer is an ethylene-co-vinylacetate-co-maleic anhydride polymer (EVA-MA polymer). For example, the mixture can comprise the EVA-MA polymer in an amount of about 90 wt. % to about 99.5 wt. % and an amine functionalized lubricant in an amount of about 0.5 wt. % to about 10 wt. %. Examples of suitable amine functionalized lubricants include oleamide, erucamide, and ethylene bis-oleamide. The at least one self-lubricated parts can be a catheter tube, an introducer tip, or a flexible tip, which has a coefficient of friction of about 0.3 or preferably 0.2 or less.

The catheters and/or the at least one self-lubricated parts (e.g., catheter tubes, introducer tips or flexible tips) disclosed herein also may have a lubricant or wetting agent applied to the surface of the catheter or part prior to use for the purpose of increasing lubricity on the outer surface of the catheter or part. For example, lubricants/wetting agents such as glycerol, polyethylene glycol, water and mixtures thereof may be applied to any of the catheters and parts disclosed herein. In one non-limiting example, such lubricants/wetting agents may be applied to catheters or parts made from a mixture of an amine containing lubricant and a polymer, such as any of the mixtures disclosed herein. In one particular example, glycerol may be applied to a catheter made from 95 wt. % of EVA-MA and 5 wt. % of oleamide.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
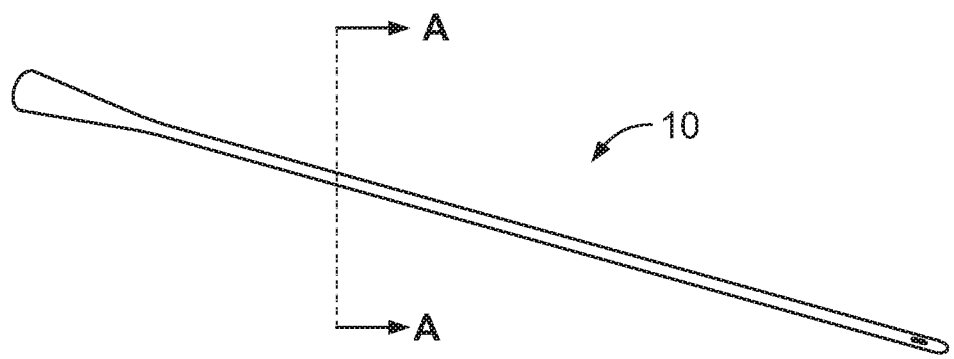
FIG. 1 is a perspective view of a catheter according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

Figure 2:
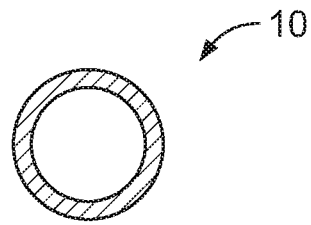
FIG. 2 is a cross-sectional illustration of the catheter of FIG. 1.

FIG. 1 illustrates a catheter 10 according to an embodiment. The catheter 10 is formed from a polymeric mixture containing a lubricant, preferably an amine containing lubricant, to provide for a self-lubricated surface for easier and less traumatic insertion of the catheter 10. The catheter 10 is also referred to as a self-lubricated catheter herein, since the lubricant is included in the catheter structure, unlike conventional catheters with a lubricant provided on the outer surface of catheters. The self-lubrication is provided as an alternate lubrication to lubricants or hydrophilic coatings commonly available for catheters. In one embodiment, the catheter 10 is a one-layer tube as shown in FIG. 2, which illustrates a cross sectional view of the catheter 10.

The catheter 10 may be formed from a mixture containing a polymer and an amine containing lubricant. Preferably, the polymer is selected from polyolefins including a functional group that can react with the amine containing lubricant. In one embodiment, the catheter 10 is formed from a mixture including about 80% to about 99.5% by weight of ethylene-co-vinylacetate-co-maleic anhydride polymer (EVA-MA) and about 0.5 wt. % to about 20 wt. % of an amine containing lubricant. Preferably, the mixture includes about 88 wt. % to about 97 wt. % of EVA-MA and about 3 wt. % to about 12 wt. % of an amine containing lubricant, and more preferably about 94 wt. % to about 96 wt. % of EVA-MA and about 4 wt. % to about 6 wt. % of the amine containing lubricant.

Suitable amine containing lubricants include, but are not limited to, oleamides, erucamide, ethylene bis-oleamide, oleamides driven from vegetable resources, stearamides, palmitamides, behenamides, or any combinations/blends thereof.

EXAMPLES AND TEST RESULTS

Various mixtures for catheters were prepared from combinations of four different polymers and three different amine containing lubricants. The polymer and lubricant combinations were melt blended in a twin screw extruder at a temperature between about 90° C. and about 170° C.

Example 1

In this first Example, each mixture included one of the polymers and one of the amine containing lubricants at 5 wt. % and 10 wt. %. Sample laces were made using the mixtures and the coefficient of friction for each sample was measured and compared against samples made without any lubricant, and gel lubricated or a hydrophilic coated catheter samples. The polymers used in the mixtures were EVA-MA polymer, ethylene-co-vinylacetate (EVA), thermoplastic polyurethane (TPU), and thermoplastic olefin elastomer (TPE). The lubricants included in the mixtures were an oleamide (OR) (Crodamide® OR supplied by Croda), an erucamide (ER) (Crodamide® ER supplied by Corda), and an ethylene bis-oleamide (EBO) (Crodamide® EBO supplied by Corda).

Six different mixtures including EVA-MA polymer were prepared. The EVA-MA polymer mixtures included: 1) a mixture of about 95 wt. % EVA-MA and about 5 wt. % ER; 2) a mixture of about 95 wt. % EVA-MA and about 5 wt. % EBO; 3) a mixture of about 95 wt. % EVA-MA and about 5 wt. % OR; 4) a mixture of about 90 wt. % EVA-MA and about 10 wt. % ER; 5) a mixture of about 90 wt. % EVA-MA and about 10 wt. % EBO; and 6) a mixture of about 90 wt. % EVA-MA and about 10 wt. % OR.

Six different mixtures including EVA polymer were also prepared. The EVA polymer mixtures included: 1) a mixture of about 95 wt. % EVA and about 5 wt. % ER; 2) a mixture of about 95 wt. % EVA and about 5 wt. % EBO; 3) a mixture of about 95 wt. % EVA and about 5 wt. % OR; 4) a mixture of about 90 wt. % EVA and about 10 wt. % ER; 5) a mixture of about 90 wt. % EVA and about 10 wt. % EBO; and 6) a mixture of about 90 wt. % EVA and about 10 wt. % OR.

Six different mixtures including TPE were also prepared. The TPE mixtures included: 1) a mixture of about 95 wt. % TPE and about 5 wt. % ER; 2) a mixture of about 95 wt. % TPE and about 5 wt. % EBO; 3) a mixture of about 95 wt. % TPE and about 5 wt. % OR; 4) a mixture of about 90 wt. % TPE and about 10 wt. % ER; 5) a mixture of about 90 wt. % TPE and about 10 wt. % EBO; and 6) a mixture of about 90 wt. % TPE and about 10 wt. % OR.

Further, Six different mixtures including TPU were prepared. The TPU mixtures included: 1) a mixture of about 95 wt. % TPU and about 5 wt. % ER; 2) a mixture of about 95 wt. % TPU and about 5 wt. % EBO; 3) a mixture of about 95 wt. % TPU and about 5 wt. % OR; 4) a mixture of about 90 wt. % TPU and about 10 wt. % ER; 5) a mixture of about 90 wt. % TPU and about 10 wt. % EBO; and 6) a mixture of about 90 wt. % TPU and about 10 wt. % OR.

Figure 6:
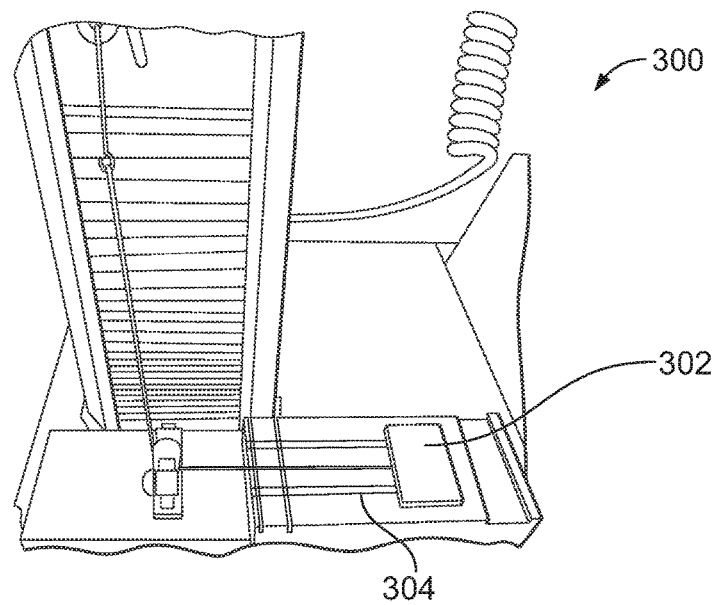
FIG. 6 is a perspective view of the test set-up used to measure the coefficient of friction in certain Examples.
Figure 7:
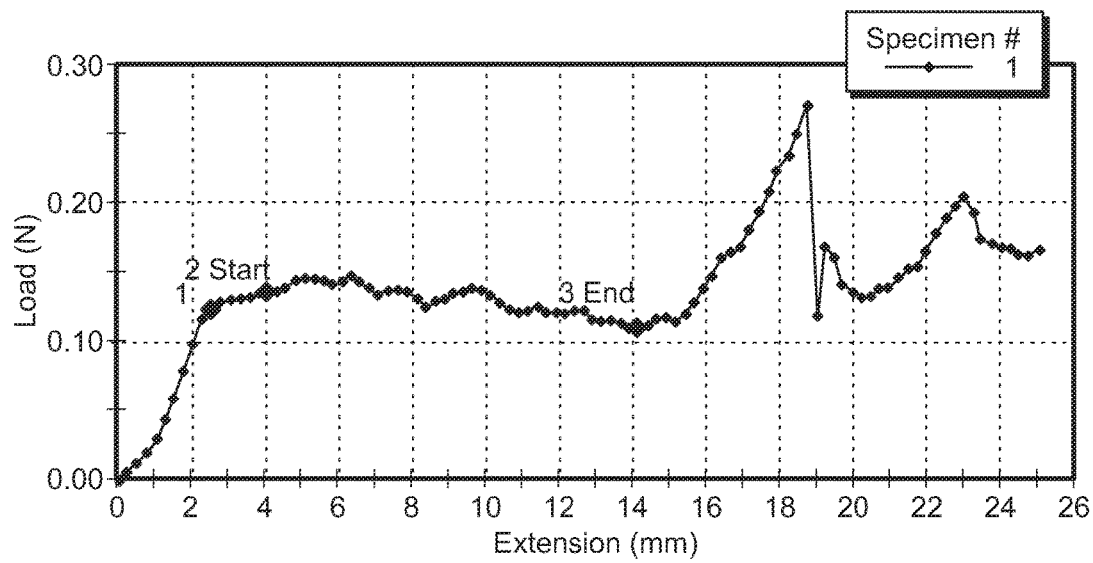
FIG. 7 is a graphical illustration of an example data output from the testing conducted on the test set-up shown in FIG. 6.

Sample tubings or laces were made using each of the mixtures and their coefficients of friction (CoF) were measured using a modified version of ASTM D1894. A picture of a test set-up used to measure CoF of the samples is shown in FIG. 6. The test set-up 300 includes a sliding sled 302. The sliding sled 302 is made of polished stainless steel 316L and has dimensions of 45 mm×30 mm×5 mm. The sled 302 weighted about 0.51N is pulled over two sample tubings (one of which is designated with reference number 304) having a length of about 120 mm at a constant speed of about 2.5 mm/s. The load required to pull the sled over the sample tubings 304 are recorded using a universal tensile testing machine equipped with a 10N load cell. CoF values are calculated from the ratio of the applied loads to the recorded loads when the sled 302 has steadily traveled about 10 mm over the sample tubings 304. For the purpose of this application, these values are considered to be steady-state CoF. An example data output from the test set-up 300 is shown in FIG. 7. Samples were also made using each of the polymers without a lubricant (i.e. EVA-MA, EVA, TPE, and TPU) and their CoF were measured. At least five test runs were conducted and measurements were taken for each sample, and an average CoF value was calculated for each sample and summarized in Table 1.

TABLE 1

Average CoF for Sample Catheters Including Amine Containing Lubricants

| Type of polymer | Type and Amount of Amine Containing Lubricant | | | | | | |
|---|---|---|---|---|---|---|---|
| | 5 wt. % ER | 5 wt. % EBO | 5 wt. % OR | 10 wt. % ER | 10 wt. % EBO | 10 wt. % OR | No lubricant |
| EVA-MA | 0.14 | 0.10 | 0.09 | 0.14 | 0.19 | 0.14 | 1.09 |
| EVA | 0.36 | 0.18 | 0.21 | 0.21 | 0.53 | 0.13 | 0.71 |
| TPE | 0.13 | 0.16 | 0.21 | 0.35 | 0.13 | 0.17 | 0.25 |
| TPU | 0.43 | 0.38 | 0.13 | 0.28 | 0.35 | 0.20 | 0.82 |

CoF for a sample including a gel (Medical Service Self Cath Set Travel, lubricated with a sterile lubricant commonly used in intermittent catheterization—Endosgel®) and a sample including a hydrophilic coating (Hollister's VaPro® product, having a polyvinylpyrrolidone (PVP)-based coating) were also measured. The sample including a gel had a CoF of 0.38, and the sample including a hydrophilic coating had a CoF of 0.02.

As shown in Table 1, the EVA-MA samples including an amine containing lubricant had the lowest CoF measurements with all of the samples measuring under 0.2. Further, the CoF measurements of the EVA-MA samples including an amine containing lubricant were lower than that of the gel lubricated samples. Although, the sample including a hydrophilic coating still provided a surface with a lower CoF than the EVA-MA samples including an amine containing lubricant, the EVA-MA samples including an amine containing lubricant provide for a good alternative lubricated catheter that is easier to handle. Further, the self-lubricated catheter provides other advantages over gel lubricated and hydrophilic coated catheters. For example, the self-lubricated catheter does not dry out during duration of use, does not require special packaging, and is ready for use after sterilization, eliminating special preparation required for hydrophilic coated catheters to activate the coating.

Example 2

A first set of tubes having outer diameters between 3 to 4 mm were made from EVA-MA. The EVA-MA used in this Example was supplied by Arkema under the trade name Orevac™ 18211 and had a Shore A hardness of 64 A. A second set of tubes having outer diameters between 3 to 4 mm were made from a mixture of about 95 wt. % EVA-MA and about 5 wt. % OR.

In this Example, the CoF was measured using the modified version of ASTM D1894 on the test set-up as described above. At least five test runs were conducted and measurements were taken for each sample, and an average CoF value was calculated for each sample and summarized in Table 2.

TABLE 2

Average CoF for Sample Tubes

| Sample Tubes | CoF |
| --- | --- |
| EVA-MA | 0.712 |
| 95 wt. % EVA-MA/5 wt. % OR | 0.285 |

Example 3

Tubes having diameters between about 3 to 4 mm were made from a mixture of about 95 wt. % EVA-MA and about 5 wt. % OR. The tubes were soaked in glycerol for five minutes and then were hung to dry for 30 seconds to remove excess liquids. The CoF of the tubes was measured using the modified version of ASTM D1894 on the test set-up as described above. At least five test runs were conducted and measurements were taken for each run, and an average CoF value was calculated and summarized in Table 3.

TABLE 3

Average CoF for Tubes Soaked in Glycerol for 5 Minutes

| Sample Tubes | CoF |
| --- | --- |
| 95 wt. % EVA-MA/5 wt. % OR | 0.061 |

Example 4

A first set of tubes having outer diameters between 3 to 4 mm were made from EVA-MA. The EVA-MA used in this Example was supplied by Arkema under the trade name Orevac™ 18211 and had a Shore A hardness of 64 A. A second set of tubes having outer diameters between 3 to 4 mm were made from a mixture of about 95 wt. % EVA-MA and about 5 wt. % OR.

The CoF of the sample tubes was measured using a Harland Friction Tester Model FTS5500. Mandrels were inserted into 127 mm section of each of the sample tubes. During friction testing, the tubes were clamped between two pieces of silicone rubber at 100 g load. Each of the tubes was pulled through the two pieces of silicone rubber at a speed of 10 mm/s. The silicone rubber had a Shore hardness of 60 A. The force required to pull about 80 mm of each of the tubes through the two pieces of silicone rubber was measured and recorded using a universal tensile tester equipped with 200 N load cell. The CoF value was calculated from the ratio of recoded to applied loads (i.e., the recorded load divided by the applied load) when steady state was reached. At least five test runs were conducted and measurements were taken for each sample, and an average CoF value was calculated for each sample and summarized in Table 4.

TABLE 4

Average CoF for Tubes Measured Against Silicone Rubber

| Sample Tubes | CoF |
| --- | --- |
| EVA-MA | >0.86 |
| 95 wt. % EVA-MA/5 wt. % OR | 0.481 |

Example 5

A first set of tubes having outer diameters between 3 to 4 mm were made from EVA-MA. The EVA-MA used in this Example was supplied by Arkema under the trade name Orevac™ 18211 and had a Shore A hardness of 64 A. A second set of tubes having outer diameters between 3 to 4 mm were made from a mixture about 95 wt. % EVA-MA and about 5 wt. % OR.

The tubes were soaked in glycerol for five minutes and then were hung to dry for 30 seconds to remove excess liquids. The CoF of each tube was measured at T=0 minutes after the 30 seconds of drying. The CoF was measured against silicone rubber on a Harland Friction Tester as described above. The tubes were then hung in a conditioning oven at 23° C. and 50% relative humidity (RH) and were retested at T=10 minutes, T=20 minutes and T=30 minutes after the initial drying. Between each test the clamping pads of the Harland Friction Tester were cleaned down with a damp wipe and then a dry wipe to remove any residue of liquid. An average of 5 samples per each test was used and their average CoF values are shown in Table 5.

TABLE 5

CoF of Tubes Soaked in Glycerol Against Silicone Rubber

| Sample | T = 0 mins | T = 10 mins | T = 20 mins | T = 30 mins |
| --- | --- | --- | --- | --- |
| EVA- MA | 0.275 | not measured | 0.361 | 0.309 |
| 95 wt. % EVA-MA/5 wt. % OR | 0.240 | 0.269 | 0.252 | 0.262 |

Figure 3:
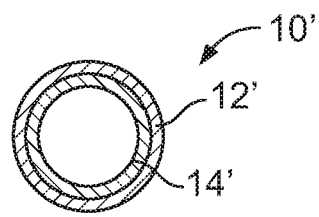
FIG. 3 is a cross-sectional illustration of a multilayer catheter according to another embodiment.

FIG. 3 shows a cross sectional view of a catheter 10' according to an alternative embodiment. The catheter 10' includes an outer layer 12' and an inner layer 14'. The outer layer 12' is formed from a mixture including a polymer and an amine containing lubricant, similar to the catheter 10 of the previously discussed embodiment. The outer layer 12' is preferably formed from a mixture including about 90 wt. % to about 95 wt. % EVA-MA polymer and about 5 wt. % to about 10 wt. % of an amine containing lubricant, such as an oleamide, an erucamide, and an ethylene bis-oleamide, and has CoF of less than 0.3, preferably less than 0.2. The outer layer 12' is configured to provide a lubricated surface for easier and less traumatic insertion and withdraw of the catheter. The inner layer 14' is formed from a suitable polymer that is compatible with the polymer in the outer layer 12', such that the outer layer 12' and the inner layer 14' are securely bound to each other when they are coextruded. For example, when the outer layer 12' is formed from a mixture including EVA-MA and an amine containing lubricant, the inner layer 14' can be formed from EVA-MA, EVA, suitably functionalized TPE, amide-ethylene oxide copolymers, or TPU.

Figure 4:
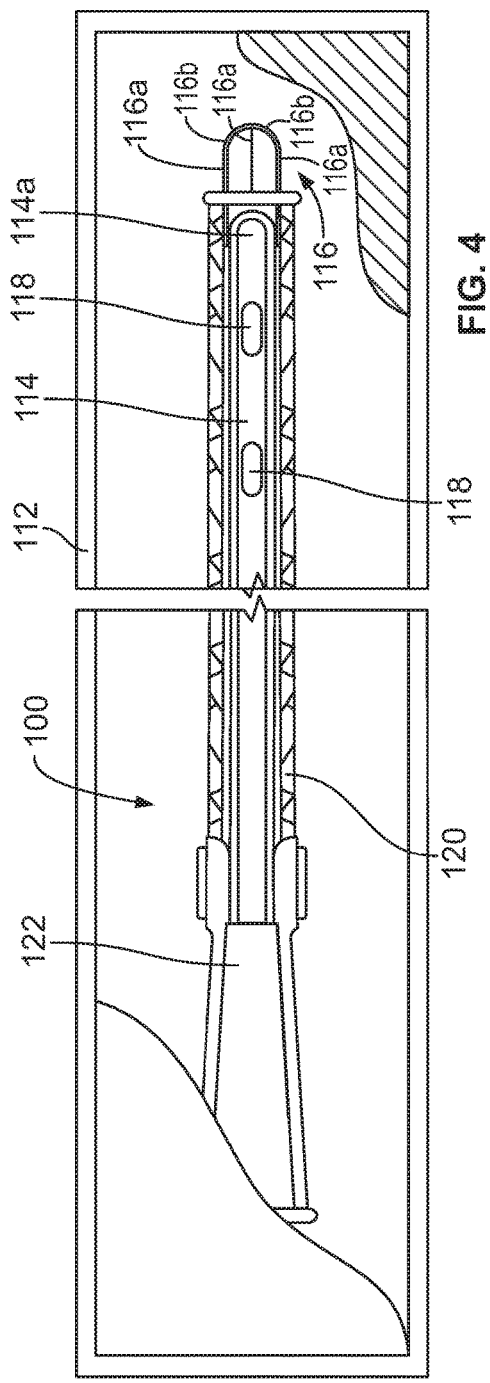
FIG. 4 is a top plan view, partially broken away of a vapor hydrated packaged hydrophilic catheter assembly including an introducer tip according to an embodiment.

In some embodiments, a catheter includes a part or parts that are self-lubricated. For example, a catheter can include an introducer tip, a tip portion, and/or a tubular body formed from a mixture containing a polymer and an amine containing lubricant. FIG. 4 shows a catheter assembly 100 including an introducer tip 116 according to an embodiment. Such a catheter is disclosed in Murray et al., U.S. Pat. No. 7,380,658, which is commonly assigned to the assignee of the present application, the entire content of which is incorporated herein by reference.

Referring to FIG. 4, the catheter assembly 100 is a hydrophilic catheter assembly that is adapted for vapor hydration within a catheter package 112 so it is ready for use when it reaches the end user. The catheter package 112 is liquid and gas impermeable and may be formed of an aluminum foil or a polymeric film. The catheter assembly 100 within the package 112 includes a catheter tube 114 having an outer surface with a hydrophilic coating on at least a portion thereof, an optional soft, rubbery introducer tip 116 adjacent an end 114a of the tube intended for pre-insertion into the urethral opening before advancement of the catheter tube, and drainage eyes 118 near the proximal insertion end 114a of the tube for draining the bladder. The catheter assembly 100 may also include a thin, flexible, collapsible sleeve 120 preferably formed of a polymeric film that is vapor permeable (although it may be liquid impermeable) and through which the hydrophilic coating can be vapor hydrated. A connector 122 in the form of a tapered funnel is located at the distal end of the catheter tube for connection by the user to a flexible drain tube leading to a urine collection device (not shown).

Figure 4A:
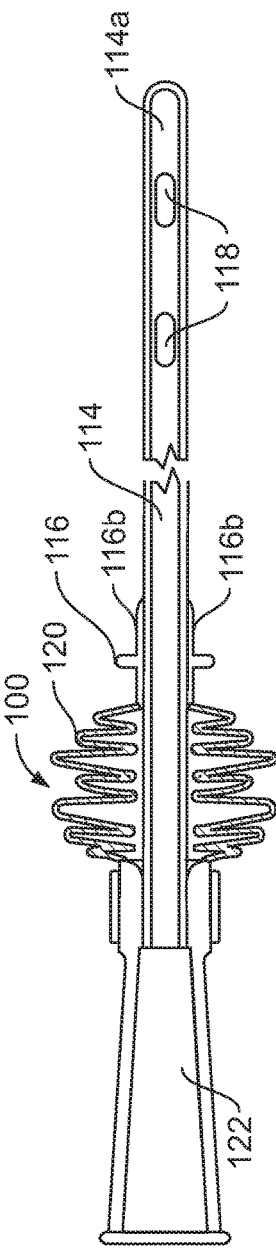
FIG. 4a is a side elevational view, partially in section, of the catheter assembly of FIG. 4.

To use the catheter assembly 100, the user may simply remove it from the package 112 by gripping the sleeve 120 and then gently insert the introducer tip 116 into the urethral opening. Preferably, the catheter assembly 100 is gripped by the sleeve 120 in one hand for advancement of the formed tip 114a of the tube 114 into and through the introducer tip 116. The introducer tip 116 has a plurality of crossed slits 116a defining a circumferential array of flaps 116b that flex outwardly to form an opening for allowing passage of the tube 114 therethrough. Thereafter, the tube is gently advanced by using the other hand to grip the tube between wall portions of the sleeve and urge the tube forwardly or proximally. As the tube 114 advances through the urethral opening into the body, the sleeve 120 will crumple adjacent the funnel 122 of the catheter assembly 100 as shown in FIG. 4a.

During manufacture, the catheter tube 114 is attached to the funnel 122 and it receives a hydrophilic coating on its outer surface. The flexible hydrogel sleeve 120 is then placed over the tube 114 and the introducer tip 116 is added to complete the catheter assembly 100. The sleeve 120 is attached either to the funnel 122 or to the introducer tip 116, or to both. In prior art, an introducer tip is typically formed of a TPE. Thus, unlike the catheter tube 114 having a low coefficient of friction provided by a hydrophilic coating, the introducer tip often caused discomfort upon insertion due to its relatively high coefficient of friction.

The catheter assembly 100 includes an improved introducer tip formed from a mixture containing a polymer and an amine containing lubricant to provide a self-lubricated introducer tip 116 having a relatively low coefficient of friction. In one preferred embodiment, the introducer tip 116 is formed from a mixture including about 99.5 wt. % of a TPE and about 0.5 wt. % of an oleamide lubricant. Test results indicate that the introducer tip 116 comprising 0.5 wt. % of an oleamide lubricant has a significantly less coefficient of friction when compared to introducer tips formed from TPE alone (the introducer tip including the oleamide lubricant had a CoF of 0.13 while the introducer tip formed from TPE without the oleamide lubricant had a CoF of 0.82.) In another embodiment, the introducer tip 116 is formed from a mixture comprising about 99.5 wt. % of EVA-MA and 0.5 wt. % of the oleamide lubricant, which provide a self-lubricated surface having a CoF of about 0.09. Again, this is a significant improvement over the prior introducer tips, and also comparable to the catheter tube 114 including a hydrophilic coating, which has a CoF of about 0.02.

Other suitable amine containing lubricants, such as erucamide, ethylene bis-oleamide, oleamides driven from vegetable resources, stearamides, palmitamides, behenamides, or any combinations/blends thereof, may also be used to form a self-lubricated introducer tip according to other embodiments. Further, the self-lubricated introducer tip 116 can be provided with a catheter assembly including a self-lubricated catheter tube formed from a mixture containing a polymer and an amine containing lubricant, such as the self-lubricated catheter 10 of the previously described embodiments.

Figure 5:
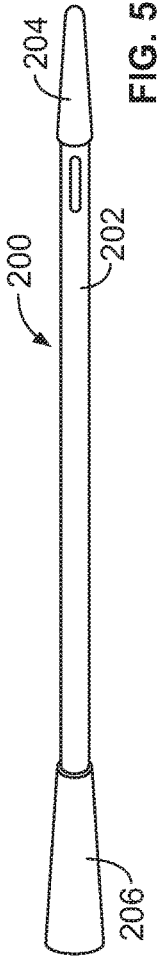
FIG. 5 is a perspective view of a catheter assembly including a flexible tip according to an embodiment.

FIG. 5 shows a catheter 200 according to yet another embodiment. The catheter 200 generally includes a catheter tube 202, a flexible tip 204, and a funnel 206. In this embodiment, the catheter tube 202 and/or the flexible tip 204 can be formed of a mixture of a polymer and an amine containing lubricant.

The self-lubricated flexible tip 204 can enhance pushability and navigation of the catheter 200 by providing a flexible tip having a low coefficient of friction. Preferably, the flexible tip 204 is formed from a mixture comprising about 90 wt. % to about 99.5 wt. % of a soft polymer, and about 0.5 wt. % to about 10 wt. % of an amine containing lubricant. Suitable soft polymers include, but are not limited to, EVA, PVC and TPE, which has Shore A hardness of about 50 to about 60. In one example, a flexible tip is injection molded using a mixture comprising about 95 wt. % of EVA and about 5 wt. % of an oleamide type polymeric lubricant to make a self-lubricated flexible tip having a CoF of about 0.2. In another example, a self-lubricated flexible tip is injection molded using a mixture comprising about 99.5 wt. % EVA-MA and about 0.5 wt. % of an oleamide lubricant, which has a CoF of about 0.09. Other suitable amine containing lubricants, such as erucamide, ethylene bis-oleamide, oleamides driven from vegetable resources, stearamides, palmitamides, behenamides, or any combinations/blends thereof, may also be used for the self-lubricated flexible tip.

The self-lubricated flexible tip 204 can be used with a catheter tube including a hydrophilic coating, such as the catheter tube 114 of the above described catheter assembly 100. Alternatively, the self-lubricated flexible tip 204 can also be used with a self-lubricated catheter tube 202 formed from a mixture comprising a polymer and an amine containing lubricant.

A self-lubricated catheter or self-lubricated parts of a catheter assembly according to various embodiments provides a surface having a significant reduced coefficient of friction, which are comparable to gel lubricated surfaces or surfaces including a hydrophilic coating. A surprisingly significant reduction in coefficient of friction has been achieved by adding a relatively small amount of an amine containing lubricant to a polymer via a simple melt processing during forming of a self-lubricated catheter or self-lubricated parts of a catheter, which provides permanent lubricity without drying out or requiring a special coating activation step or packaging.

Furthermore, the catheters and/or the at least one self-lubricated parts (e.g., catheter tubes, introducer tips or flexible tips) disclosed herein also may have a lubricant or wetting agent applied to the surface of the catheter or part prior to use for the purpose of increasing lubricity on the outer surface of the catheter or part. For example, lubricants/wetting agents such as glycerol, polyethylene glycol, water and mixtures thereof may be applied to the outer surface any of the catheters and parts disclosed herein. In one non-limiting example, such lubricants/wetting agents may be applied to catheters or parts made from a mixture of an amine containing lubricant and a polymer, such as any of the mixtures disclosed herein. In one particular example, glycerol may be applied to a catheter made from 95 wt. % of EVA-MA and 5 wt. % of oleamide.

In the present disclosure, the words "a" or "an" are to be taken to include both the singular and the plural. Conversely, any reference to plural items shall, where appropriate, include the singular. All of the concentrations noted herein as percentage are percent by weight unless otherwise noted.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An intermittent urinary catheter comprising:
   a catheter shaft formed from a mixture, the mixture comprising:
   an amine containing lubricant in an amount of about 0.05 percent by weight (wt. %) to about 20 wt. % of the mixture;
   a polymer, the polymer having a functional group that can react with an amine functional group of the amine containing lubricant; and
   the catheter shaft having an outer surface formed from the mixture wherein the outer surface has a coefficient of friction of less than about 0.3.

2. The catheter of claim 1, wherein the polymer is an ethylene-co-vinylacetate-co-maleic anhydride polymer (EVA-MA polymer).

3. The catheter of claim 2, wherein the amine containing lubricant is an oleamide, and wherein the mixture includes the EVA-MA polymer in an amount of about 90 wt. % to about 95 wt. % and the oleamide in an amount of about 5 wt. % to about 10 wt. %.

4. The catheter of claim 3, wherein the mixture includes the EVA-MA polymer in an amount of about 95 wt. % and the oleamide in an amount of about 5 wt. %.

5. The catheter of claim 2, wherein the amine containing lubricant is a erucamide, and wherein the mixture includes the EVA-MA polymer in an amount of about 90 wt. % to about 95 wt. % and the erucamide in an amount of about 5 wt. % to about 10 wt. %.

6. The catheter of claim 5, wherein the mixture includes the EVA-MA polymer in an amount of about 95 wt. % and the erucamide in an amount of about 5 wt. %.

7. The catheter of claim 2, wherein the amine containing lubricant is an ethylene bis-oleamide, and wherein the mixture includes the EVA-MA polymer in an amount of about 90 wt. % to about 95 wt. % and the ethylene bis-oleamide in an amount of about 5 wt. % to about 10 wt. %.

8. The catheter of claim 7, wherein the mixture includes the EVA-MA polymer in an amount of about 95 wt. % and the ethylene bis-oleamide in an amount of about 5 wt. %.

9. A multilayer intermittent urinary catheter shaft, comprising:
   a coextruded tube including:
   an outer extruded layer formed from a mixture including:
   an amine containing lubricant in an amount of about 0.05 wt. % and to 20 wt. % of the mixture; and
   a first polymer, the first polymer having a functional group that can react with an amine functional group of the amine containing lubricant;
   an inner extruded layer, the inner layer formed from a second polymer; and
   the outer layer defining an outer surface formed from the mixture wherein the outer surface has a coefficient of friction of less than about 0.3.

10. The multilayer catheter of claim 9, wherein the first polymer is an EVA-MA polymer.

11. The multilayer catheter of claim 10, wherein the amine containing lubricant is an oleamide, and wherein the mixture includes the EVA-MA polymer in an amount of about 90 wt. % to about 95 wt. % and the oleamide in an amount of about 5 wt. % to about 10 wt. %.

12. The multilayer catheter of claim 11, wherein the mixture includes the EVA-MA polymer in an amount of about 95 wt. % and the oleamide in an amount of about 5 wt. %.

13. The multilayer catheter of claim 10, wherein the amine containing lubricant is a erucamide, and wherein the mixture includes the EVA-MA polymer in an amount of about 90 wt. % to about 95 wt. % and the erucamide in an amount of about 5 wt. % to about 10 wt. %.

14. The multilayer catheter of claim 13, wherein the mixture includes the EVA-MA polymer in an amount of about 95 wt. % and the erucamide in an amount of about 5 wt. %.

15. The multilayer catheter of claim 10, wherein the amine containing lubricant is an ethylene bis-oleamide, and wherein the mixture includes the EVA-MA polymer in an amount of about 90 wt. % to about 95 wt. % and the ethylene bis-oleamide in an amount of about 5 wt. % to about 10 wt. %.

16. The multilayer catheter of claim 15, wherein the mixture includes the EVA-MA polymer in an amount of about 95 wt. % and the ethylene bis-oleamide in an amount of about 5 wt. %.

17. The multilayer catheter of claim 9 wherein the second polymer is selected from the group consisting of EVA-MA polymer, ethylene-co-vinylacetate polymer, thermoplastic polyurethane polymer, and functionalized thermoplastic olefin elastomer.

18. An intermittent catheter assembly including at least one self-lubricated part, the at least one self-lubricated part comprising:
   a functionalized polymer containing a first functional group; and
   a functionalized lubricant containing a second functional group that can react with the first functional group,
   wherein the functionalized polymer and the functionalized lubricant are melt mixed to form a mixture, and wherein the at least one self-lubricated part includes an outer surface that is formed from the mixture and has a coefficient of friction of less than 0.3.

19. The catheter assembly of claim 18, wherein the functionalized polymer is an anhydride functionalized polymer, and the functionalized lubricant is an amine functionalized lubricant.

20. The catheter assembly of claim 19, wherein the mixture includes the amine functionalized lubricant in an amount of about 0.05 wt.% to about 20 wt.% of the mixture.

21. The catheter assembly of claim 18, wherein the polymer is an ethylene-co-vinylacetate-co-maleic anhydride polymer (EVA-MA polymer).

22. The catheter assembly of claim 18, wherein the functionalized polymer is an EVA-MA polymer and the functionalized lubricant is an oleamide, and wherein the mixture includes the EVA-MA polymer in an amount of about 90 wt.% to about 99.5 wt.% and the oleamide in an amount of about 0.5 wt.% to about 10 wt.%.

23. The catheter assembly of claim 22, wherein the mixture includes the EVA-MA polymer in an amount of about 95 wt.% and the oleamide in an amount of about 5 wt.%.

24. The catheter assembly of claim 18, wherein the functionalized polymer is an EVA-MA polymer and the functionalized lubricant a erucamide, and wherein the mixture includes the EVA-MA polymer in an amount of about 90 wt.% to about 95 wt.% and the erucamide in an amount of about 5 wt.% to about 10 wt.%.

25. The catheter assembly of claim 24, wherein the mixture includes the EVA-MA polymer in an amount of about 95 wt.% and the erucamide in an amount of about 5 wt.%.

26. The catheter assembly of claim 18, wherein the functionalized polymer is an EVA-MA polymer and the functionalized lubricant an ethylene bis-oleamide, and wherein the mixture includes the EVA-MA polymer in an amount of about 90 wt.% to about 95 wt.% and the ethylene bis-oleamide in an amount of about 5 wt.% to about 10 wt.%.

27. The catheter assembly of claim 26, wherein the mixture includes the EVA-MA polymer in an amount of about 95 wt.% and the ethylene bis-oleamide in an amount of about 5 wt.%.

28. The catheter assembly of claim 18 wherein, the at least one self-lubricated part is selected from the group of a catheter tube, an introducer tip and a flexible tip.

* * * * *